United States Patent [19]

Sato

[11] Patent Number: 5,268,732
[45] Date of Patent: Dec. 7, 1993

[54] APPARATUS FOR MEASURING SPECTRAL TRANSMISSIVITY OF OPTICAL FIBER

[75] Inventor: Tatsumi Sato, Kyoto, Japan
[73] Assignee: Shimadzu Corporation, Kyoto, Japan
[21] Appl. No.: 958,690
[22] Filed: Oct. 9, 1992
[30] Foreign Application Priority Data
Dec. 7, 1991 [JP] Japan ............................ 3-349592
[51] Int. Cl.[5] ....................... G01N 21/27; G01N 21/59
[52] U.S. Cl. .................................... 356/73.1; 250/228
[58] Field of Search ............... 356/73.1, 236; 250/228
[56] References Cited
U.S. PATENT DOCUMENTS
4,183,666 1/1980 Tahara et al. ..................... 356/73.1

*Primary Examiner*—Vincent P. McGraw
*Attorney, Agent, or Firm*—Heller, Ehrman, White & McAuliffe

[57] ABSTRACT

An integrating sphere has two openings, at which light-receiving and light-emitting ends of an optical fiber sample are attached. A light-receiving opening is provided opposite one of these openings, and another light-receiving opening opposite from none of those other openings. A monochromatic light beam from a source such as a spectroscope is passed through a lens or the like to be made convergent and introduced into the integrating sphere through each of the light-receiving openings. The difference in the optical path length between the two measurements is entirely due to the presence or absence of the optical fiber sample, and the spectral transmissivity of the sample can be measured accurately.

6 Claims, 3 Drawing Sheets

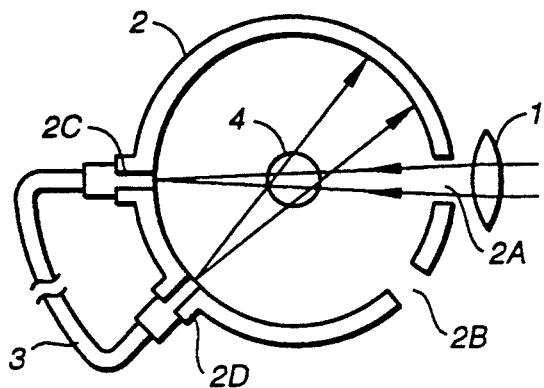
FIG._1A
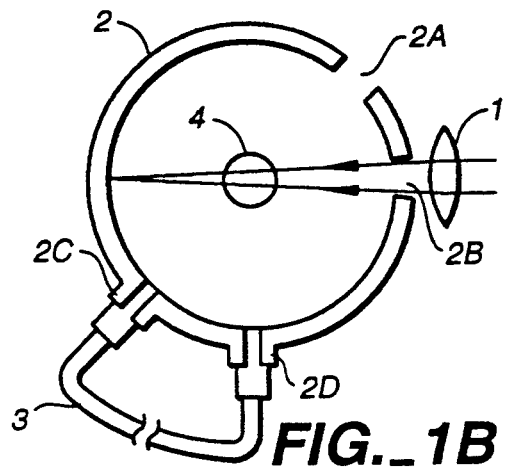
FIG._1B
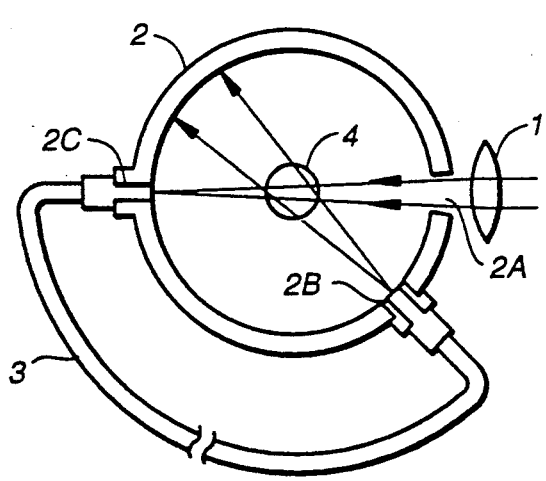
FIG._2A
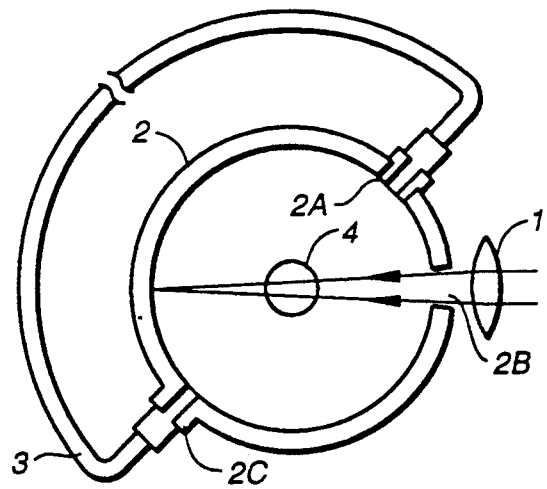
FIG._2B

FIG._3A
*(PRIOR ART)*
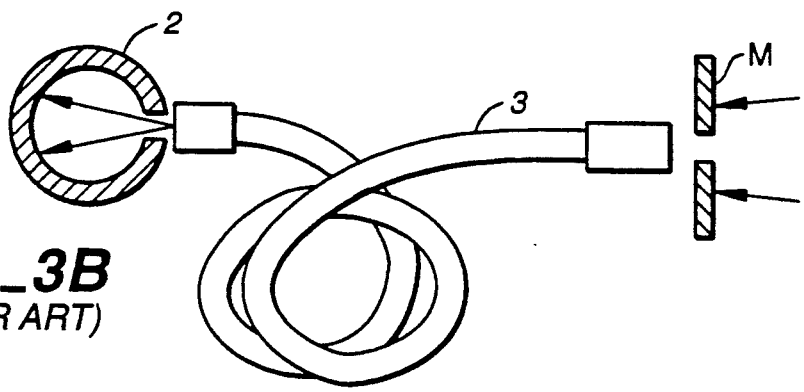
FIG._3B
*(PRIOR ART)*
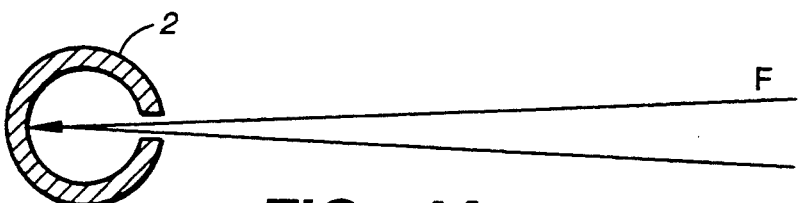
FIG._4A
*(PRIOR ART)*
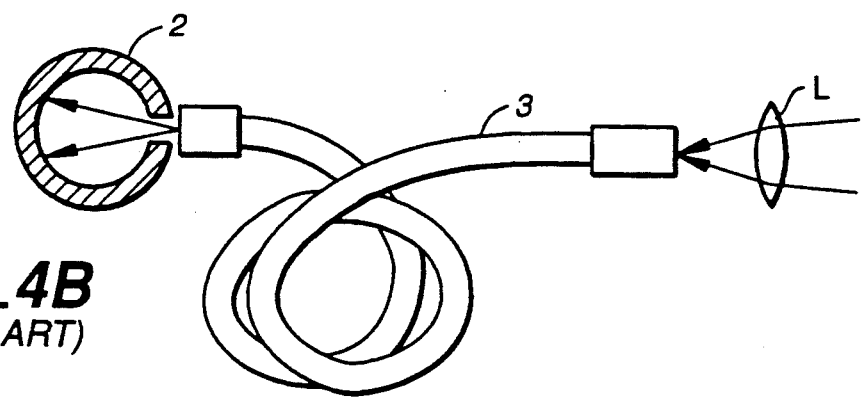
FIG._4B
*(PRIOR ART)*

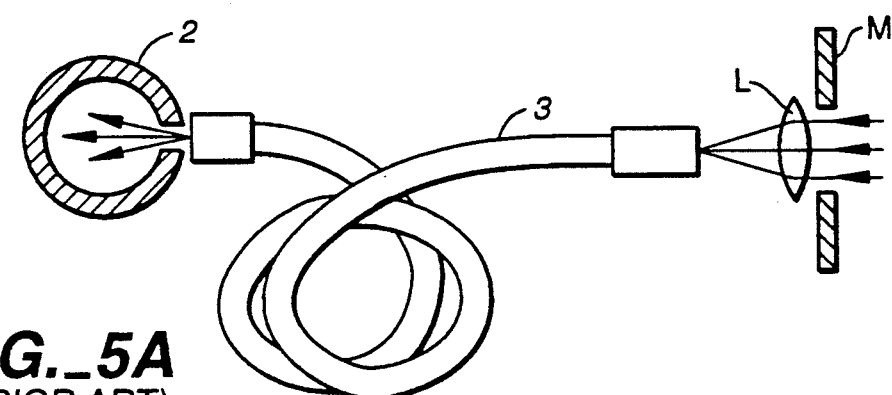
FIG._5A
(PRIOR ART)
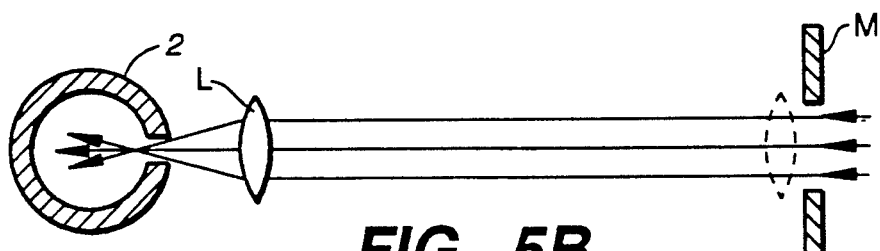
FIG._5B
(PRIOR ART)

5,268,732

APPARATUS FOR MEASURING SPECTRAL TRANSMISSIVITY OF OPTICAL FIBER

BACKGROUND OF THE INVENTION

This invention relates to an apparatus for measuring the spectral transmissivity of optical fiber.

Apparatus for measuring the transmissivity of optical fiber, either dedicated for the purpose or standardized as a peripheral of a spectro-photometer, have not been commercially available. It has been customary for the user, therefore, to either have an apparatus specially made or design one for himself. There has not been even a standard method of measuring the transmissivity of optical fiber. Apparatus thus designed and used by individual users for measuring the transmissivity of optical fiber are structured basically as shown in FIG. 3 or 4.

In general, transmissivity of a given material is determined by measuring the light value of an incoming monochromatic test beam with a sample placed in its optical path and by removing it therefrom to obtain the so-called 100% transmissivity. According to the prior art method illustrated in FIG. 3, a mask M, having an aperture with diameter smaller than the bundle diameter of an optical fiber sample 3 to be measured, is placed within the optical path of an outgoing beam from a spectro-photometer, and an integrating sphere 2 with a light-receiving window is set at a certain distance from this mask M such that the outgoing beam from the spectro-photometer can be introduced thereinto. For the measurement of the 100% transmissivity, the space between the mask M and the integrating sphere 2 is left empty as shown in FIG. 3A. For determining the transmissivity of the optical fiber sample 3, the light-receiving end of the sample 3 is placed close to the opening in the mask M and its light-emitting end is place closed to the light-receiving window of the integrating sphere 2, as shown in FIG. 3B. The distance between the mask M and the integrating sphere 2, therefore, should be sufficiently large for placing the sample 3 in between.

According to the method illustrated in FIG. 4, the entire outgoing beam from a spectro-photometer is made incident directly into an integrating sphere 2, as shown in FIG. 4A, for the measurement of 100% transmissivity. For the measurement of transmissivity of an optical fiber sample 3, the same outgoing beam from the spectro-photometer is caused to converge into the light-receiving end of the sample 3 by using a lens L or the like, as shown in FIG. 4B. The light emitting end of the sample 3 is placed close to the light-receiving window of the integrating sphere 2, as shown in FIG. 4B. It now goes without saying, regarding the prior art methods described above, that an identical beam must be directed, at one time, into the integrating sphere 2 for the measurement of the 100% transmissivity and, at another time, into the sample 3 of which the transmissivity is to be measured. When a spectro-photometer is used, the sample is usually placed inside a sample chamber. When the transmissivity of optical fiber is to be measured, however, since the optical fiber cannot be placed inside the sample chamber, it is necessary to set is outside the sample chamber and to guide the light out of the chamber. In this situation, the diameter of the outgoing beam (indicated by letter F in FIGS. 3A and 4A) from a spectroscope outside the sample chamber is greater than the bundle diameter (about 1-3mm) of the optical fiber. In the example of FIG. 3, the mask M is used for the purpose of providing and introducing a beam of the same diameter into the integrating sphere 2 for the measurement of 100% transmissivity and into the optical fiber 3 for the measurement of its transmissivity. In the example of FIG. 4, the entire outgoing beam from the spectroscope is made incident into the integrating sphere, but a convergent lens L is necessary to make it totally introduced into optical fiber sample 3. By the method of FIG. 3, the signal-to-noise ratio is not good because only a limited portion of the outgoing beam from the spectro-photometer is utilized and hence the available quantity of light is reduced. The use efficiency of light is better with the method of FIG. 4, but since the lens L is inserted only when the transmissivity of the sample is measured, what is actually measured is the combined transmissivity of both the lens L and the optical fiber sample 3. In other words, the method according to FIG. 4 has the disadvantage of reduced accuracy.

As described in Japanese Patent Application 2-262578 and illustrated in FIG. 5, the present inventor proposed a new method whereby a converging lens L is inserted for the measurement of both a sample (FIG. 5A) and the 100% transmissivity (FIG. 5B). The same lens L can be placed interchangeably at two different positions along the optical path of the outgoing beam from the spectro-photometer. By this method, the difference in optical path length between the two measurements does not include the transmissivity of the lens L, and the same amount of light can be made incident into the integrating sphere for the measurement of the 100% transmissivity and into a sample for the measurement of its transmissivity. Thus, both the signal-to-noise ratio and the accuracy of measurement can be improved. By this method, however, the optical fiber sample must be placed with its end portions positioned in a collinear relationship and hence a relatively large space is required between the mask M and the integrating sphere 2. Another disadvantage of this method is that the converging lens L must be moved between the two measurements.

It is therefore an object of the present invention to provide an apparatus, serving as a peripheral of a spectro-photometer, for measuring the true spectral transmissivity, in principle, of optical fiber by making use of light with improved efficiency.

SUMMARY OF THE INVENTION

An apparatus according to the present invention for measuring the spectral transmissivity of optical fiber, with which the above and other objects can be accomplished, may be characterized as comprising an integrating sphere having two openings, each for the attachment thereto of one of the ends of an optical fiber sample. Two other openings, referred to as light-receiving openings, are provided for admitting incident light therethrough, one of these openings being positioned opposite to one of the openings for attaching the optical fiber and the other being opposite to none of the other openings. An optical element, such as a lens, for converging a light beam is provided and the integrating sphere is supported rotatably around an axis which passes its center such that one or the other of the light-receiving openings can be selectably positioned behind it. Alternatively, use may be made of an integrating sphere with only three openings, two of which being opposite to each other. The light-receiving end of the optical fiber sample is attached to one of the mutually opposite openings. The light-emitting end of the sample is attached to the opposite opening for the measurement of the 100% transmissivity and to the third opening opposite from neither of the other two openings when the transmissivity of the sample is measured.

Because of the presence of the light-converging element, the same amount of light is made incident for the measurement of both the 100% transmissivity and the transmissivity of a sample. With both ends of the optical fiber sample attached to the integrating sphere, light is made incident through the opening which is opposite to the light-receiving end of the optical fiber sample when its transmissivity is to be measured. The light, after passing through the optical fiber sample, re-enters the integrating sphere. For the measurement of the 100% transmissivity, light is made incident through a different opening so as to directly hit the inner wall of the integrating sphere. Measurements being carried out in this manner, the difference in the optical path between the two measurements is entirely due to the passage through the optical fiber. Thus, the spectral transmissivity of an optical fiber sample can be measured with high accuracy.

BRIEF DESCRIPTION OF THE DRAWING

The accompanying drawings, which are incorporated in and form a part of this specification, illustrate embodiments of the invention and, together with the description, serve to explain the principles of the invention. In the drawings:

FIGS. 1A and 1B are sectional views of an apparatus embodying the present invention respectively when the transmissivity of an optical fiber sample is measured and when the 100% transmissivity is measured;

FIGS. 2A and 2B are sectional views of another apparatus embodying the present invention respectively when the transmissivity of an optical fiber sample is measured and when the 100% transmissivity is measured;

FIGS. 3A and 3B are partially sectional views of a prior art apparatus respectively when the 100% transmissivity is measured and the transmissivity of an optical fiber sample is measured;

FIGS. 4A and 4B are partially sectional views of another prior art apparatus respectively when the 100% transmissivity is measured and the transmissivity of an optical fiber sample is measured; and FIGS. 5A and 5B are partially sectional views of still another prior art apparatus respectively when the transmissivity of an optical fiber sample is measured and when the 100% transmissivity is measured.

DETAILED DESCRIPTION OF THE INVENTION

In FIGS. 1A and 1B, which show an embodiment of the present invention, numeral 1 indicates a lens serving as an optical means for converging a monochromatic light beam from a spectroscope (not shown) and making it incident into an integrating sphere 2 through one of two light-receiving openings 2A and 2B. The integrating sphere 2 is rotatably supported around an axis which passes through its center perpendicularly to the page. The integrating sphere 2 has another opening 2C exactly opposite to one of the light-receiving openings (2A in FIGS. 1A and 1B) for attaching the light-receiving end of an optical fiber sample 3 such that the light beam which enters the integrating sphere 2 through the light-receiving opening 2A will be made incident directly into the optical fiber sample 3. There is only a wall surface with no opening opposite from the other light-receiving opening 2B such that any light entering the integrating sphere 2 through this light-receiving opening 2B will be made incident on the wall of the sphere, as shown in FIG. 1B.

The integrating sphere 2 has still another opening 2D which is for the attachment of the light-emitting end of the optical fiber sample 3 and is not opposite to either of the light-receiving openings 2A and 2B. In FIGS. 1A and 1B, numeral 4 indicates a light detector disposed at such a position inside the integrating sphere 2 that beams of light entering through the light-receiving openings 2A and 2B will not be received directly thereby but will be received thereby only after man irregular diffuse reflections.

For the measurement of the transmissivity of the sample 3, the integrating sphere 2 is oriented as shown in FIG. 1A such that the monochromatic beam of light from the spectroscope (not shown) is made convergent and guided into the integrating sphere 2 through the light-receiving opening 2A opposite to the light-receiving end of the optical fiber 2. After passing through the optical fiber 3, the light beam re-enters the interior of the integrating sphere 2 through the opening 2D. Since there is no opening opposite to the light-emitting end of the optical fiber 3, the re-entering light beam undergoes many irregular diffuse reflections inside the integrating sphere 2 and eventually measured by the detector 4.

For the measurement of the 100% transmissivity, the integrating sphere 2 is rotated around the axis of rotation to a position shown in FIG. 1B such that the converging light beam through the lens 1 will enter the integrating sphere 2 through the other of the light-receiving opening (2B). Since there is no opening opposite to this light-receiving opening 2B, the incident beam undergoes many diffuse reflections inside the sphere 2 and detected by the detector 4. The result of measurement in this case represents the hypothetical situation where the optical fiber has transmissivity of 100%. Thus, the transmissivity of the sample 3 can be obtained by comparing the results of the two measurements described above. Ideally, the light-receiving and light-emitting ends of the optical fiber 3 should be flush with the internal reflecting surface of the integrating sphere 2, but small indentations do not significantly affect the accuracy of the measurements.

FIGS. 2A and 2B illustrate another apparatus embodying the invention. Components which are substantially identical to those shown in FIGS. 1A and 1B are indicated by the same numerals.

The integrating sphere 2 according to this embodiment of the invention is characterized in that one of the two light-receiving openings 2A and 2B of the integrating sphere 2 also serves as an opening for attachment of the light-emitting end of the optical fiber sample 3. For the measurement of transmissivity of an optical fiber sample 3, its light-receiving end is attached to the opening 2C opposite to one of the light-receiving openings (2A) of the integrating sphere 2 and its light-emitting end is attached to the other of the light-receiving openings (2B) as shown in FIG. 2A. The incident light beam is passed through the lens 1 to be made convergent and enters the integrating sphere 2 through the light-receiving opening 2A. After entering and traversing the integrating sphere 2, the incident light passes through the optical fiber through its light-receiving end at the opening 2C and re-enters the integrating sphere 2 again through its light-emitting end at the other light-receiving opening 2B. Since there is no opening opposite to the light-emitting end of the optical fiber sample 3, the emitted light from the optical fiber sample 3 undergoes many diffuse reflections and is measured by the detector 4.

For the measurement of the 100% transmissivity, the light-emitting end of the optical fiber sample 3 is attached to the other of the light-receiving openings (2A), and the integrating sphere 2 is rotated such that the incoming light beam through the lens 1 will enter the integrating sphere 2 through the open one of its light-receiving openings (2B), as shown in FIG. 2B. The incident beam through the opening 2B does not reach the optical fiber sample 3, but undergoes many diffuse reflections and is measured by the detector 4. The results of these two measurements are compared to obtain the transmissivity of the sample 3.

The embodiment of the present invention illustrated in FIGS. 2A and 2B is advantageous in that the incident beam of light is first reflected at the same position (opposite to the opening 2B) on the inner wall of the integrating sphere 2 for both measurements. Thus, even if uniformity in reflectivity is lost over the inner surface of the integrating sphere after an elapse of time, the effect of such non-uniformity does not seriously affect the accuracy of measurement.

Although the present invention has been described above by way of only two embodiments, the invention is not intended to be limited by these embodiments. Many modifications and variations are considered possible on the basis of the disclosure given above. For example, although FIG. 2B shows the light-emitting end of the optical fiber attached to the opening 2B, it is not necessary to so attach the light-emitting end of the optical fiber, especially if the area of the openings 2A and 2B is negligibly small as compared to the inner surface area of the entire integrating sphere. It may also be recognized that the aforementioned rotation of the integrating sphere can be dispensed with if the monochromatic beam from a light source is split into two beams, each being adapted to be introduced into the integrating sphere through a different one of the light-receiving openings. In summary, the optical fiber sample becomes the sole source of difference in optical path length between the measurements according to the present invention.

What is claimed is:

1. An apparatus for measuring spectral transmissivity of an optical fiber sample, said apparatus comprising:
   an integrating sphere having two fiber-attaching openings each allowing an end portion of said optical fiber sample to be attached thereto, a first light-receiving opening opposite one of said two fiber-attaching openings, and a second light-receiving opening not opposite from either of said two fiber-attaching openings; and
   an optical element for converging a light beam, said optical element allowing to be placed selectably in front of said first or second light-receiving opening.

2. The apparatus of claim 1 wherein said integrating sphere is rotatable around an axis passing through its center such that said first and second light-receiving openings can be selectably placed behind said optical element.

3. The apparatus of claim 1 wherein said integrating sphere includes a light detector disposed such that light, which is introduced into said integrating sphere, is detected thereby only after many irregular diffuse reflections inside said integrating sphere.

4. An apparatus for measuring spectral transmissivity of an optical fiber sample, said apparatus comprising:
   an integrating sphere having a fiber-attaching opening allowing one end of said optical fiber sample to be attached thereto, a first light-receiving opening opposite said fiber-attaching opening, and a second light-receiving opening not opposite from either said fiber-attaching opening or said first light-receiving opening, said second light-receiving opening allowing the other end portion of said optical fiber sample to be attached thereto or detached therefrom; and
   an optical element for converging a light beam, said optical element allowing to be placed selectably in front of said first or second light-receiving opening.

5. The apparatus of claim 4 wherein said integrating sphere is rotatable around an axis passing through its center such that said first and second light-receiving openings can be selectably placed behind said optical element.

6. The apparatus of claim 4 wherein said integrating sphere includes a light detector disposed such that light, which is introduced into said integrating sphere, is detected thereby only after many irregular diffuse reflections inside said integrating sphere.

* * * * *